United States Patent [19]

Hirschbein

[11] Patent Number: 5,166,387
[45] Date of Patent: Nov. 24, 1992

[54] METHOD OF SYNTHESIZING SULFURIZED OLIGONUCLEOTIDE ANALOGS WITH THIURAM DISULFIDES

[75] Inventor: Bernard L. Hirschbein, San Francisco, Calif.

[73] Assignee: Applied Biosystems, Inc., Foster City, Calif.

[21] Appl. No.: 464,182

[22] Filed: Jan. 12, 1990

[51] Int. Cl.$^5$ .......................... C07F 9/04; C07H 21/00
[52] U.S. Cl. ................................. 558/129; 536/27; 536/55.3; 568/13; 568/14; 568/15; 548/113; 548/119
[58] Field of Search ............... 536/27, 55.3; 564/76; 568/13, 14, 15; 548/113, 119; 558/129

[56] References Cited

U.S. PATENT DOCUMENTS

| | | | |
|---|---|---|---|
| 1,413,172 | 4/1922 | Lorentz | 564/76 |
| 1,782,111 | 11/1930 | Adams et al. | 564/76 |
| 1,796,977 | 3/1931 | Bailey | 564/76 |
| 3,116,328 | 12/1963 | Cox et al. | 564/76 |
| 3,426,003 | 2/1969 | Leib et al. | 525/341 |
| 3,494,900 | 2/1970 | Morita et al. | 525/341 |
| 4,144,272 | 3/1979 | Bergomi et al. | 564/76 |
| 4,816,571 | 3/1989 | Andrus et al. | 536/27 |
| 5,003,097 | 3/1991 | Beaucage et al. | 558/129 |

OTHER PUBLICATIONS

Tolmacheva et al, J. of General Chem. of the USSR, vol. 48, pp. 982–984 (1978).
Michalski et al, Roczniki Chemii, vol. 33, pp. 247–250 (1958).
Chemical Abstracts, vol. 16, pp. 854–855 (1922).
WHO, IARC Monographs on the Evaluation of Carcinogenic Risk of Chemicals to Man, vol. 12, pp. 225–236 (1976).
Cummings et al, Indust. Engineering Chem., vol. 20, pp. 1173–1176 (1928).
Iyer et al, Nucleic Acids Research, vol. 18, pp. 2855–2859 (1990).
Rigaudy et al, IUPAC Nomenclature for Organic Chemistry, Sections A–F and H (Pergamon Press, Oxford, 1979), pp. 382–382, 337–339.
Goldwhite, Introduction to Phosphorous Chemistry, p. xii (Cambridge University Press, Cambridge, 1981).
Parker, ed. McGraw-Hill Dictionary of Chemical Terms (McGraw-Hill, New York, 1984), pp. 244–245.
Atkinson et al, in Gait ed, Oligonucleotide Synthesis: A Practical Approach (IRL Press, Oxford, 1984), pp. 35 and 50–51.
Roberts et al, Modern Organic Chemistry, pp. 642–644 (Benjamin, New York, 1967), p. 643.
Farschischi et al. (1988) Tetrahedron Letters vol. 29, No. 52, pp. 6843–6846.
Brill et al. (1988), Tetrahedron Letters, vol. 29, No. 43, pp. 5517–5520.
Brill et al. (1988) J. Am. Chem. Soc., vol. 111, pp. 2321–2322.
Matsukura et al. (1989) Proc. Natl. Acad. Sci. vol. 86, pp. 4244–4248.
Stec et al. (1984) J. Am. Chem. Soc., vol. 106, pp. 6077–6079.
Ott et al. (1987) Biochemistry, vol. 26, pp. 8237–8241.

Primary Examiner—John W. Rollins
Assistant Examiner—Gary L. Kunz
Attorney, Agent, or Firm—Stephen C. Macevicz

[57] ABSTRACT

A method for synthesizing sulfurized oligonucleotide analogs, such as phosphorothioate and phosphorodithioate analogs, is provided that employs a thiuram disulfide as a sulfurizing agent. The method of the invention may be used to sulfurize any phosphorous(III)-containing intermediate. Preferably, the method is practiced on a commercial DNA synthesizer using phosphoramidite and/or phosphorthioamidite intermediates.

5 Claims, No Drawings

METHOD OF SYNTHESIZING SULFURIZED OLIGONUCLEOTIDE ANALOGS WITH THIURAM DISULFIDES

FIELD OF THE INVENTION

The invention relates generally to the synthesis of oligonucleotides, and more particularly, to a method for sulfurizing oligonucleotides with thiuram disulfides to form phosphorothioate and/or phosphorodithioate analogs thereof.

BACKGROUND

With the development of efficient methods of synthesis, interest has arisen in the use of anti-sense oligonucleotides to treat a variety of diseases, particularly viral infections, e.g. Matsukura et al, Proc. Natl. Acad. Sci., Vol. 86, pgs. 4244-4448 (1989). An antisense oligonucleotide is a synthetic oligonucleotide of varying length, usually in the range of about 12 to 30 nucleotides, or nucleotide analogs, whose sequence is complementary to a predetermined segment of the RNA, either freshly transcribed or the messenger (mRNA), critical to some viral function. It is believed that when an antisense oligonucleotide hybridizes to its target RNA, it either blocks translation or processing of the RNA or makes it susceptible to enzymatic degradation.

One problem with this approach has been the difficulty of getting the antisense oligonucleotide to its target RNA in sufficient concentration and for sufficient duration to be effective in shutting down the synthesis of undesired proteins, e.g. viral enzymes, coat proteins, and the like. The susceptibility of the phosphodiester linkage of the oligonucleotides to nuclease digestion is believed to be an important cause of this difficulty, and has prompted the development of a variety of nucleoside oligomers linked by nuclease-resistant analogs of the natural phosphodiester bond, e.g. Miller et al, U.S. Pat. No. 4,511,713 and Ts'o U.S. Pat. No. 4,469,863 (methyl- and arylphosphonates); Miro et al, Nucleic Acids Research, Vol. 17, pgs. 8207-8219 (1989) (phosphoroselenoates); Brill et al, J. Am. Chem. Soc., Vol. 111, pg. 2321 (1989) (phosphorodithioates); and Matsukura et al, Proc. Natl. Acad. Sci., Vol. 84, pgs. 7706-7710 (1987), and Gene, Vol. 72, pgs. 343-347 (1988) (phosphorothioates).

The phosphorothioate and phosphorodithioate analogs are especially promising because they are highly nuclease-resistant, have the same charge as natural oligonucleotides, and are taken up by cells in effective amounts.

Phosphorothioates are conveniently synthesized by automated DNA synthesizers using hydrogen phosphonate chemistry, which permits the phosphonate backbone to be sulfurized in a single step off of the automated synthesizer after synthesis. This is advantageous because the phosphonate moieties are sulfurized by exposure to elemental sulfur dissolved in an organic solvent. Since the sulfur readily precipitates out of solution, the off-column sulfurization avoids costly blockages of valves and tubing of the synthesizer by sulfur precipitates. A drawback of this route of phosphorothioate synthesis is that coupling yields during chain elongation are typically lower than those obtained using phosphoramidite chemistry, Gaffney and Jones, Tett. Lett., Vol. 29, pgs. 2619-2622 (1988). The practical importance of high coupling yields is demonstrated by the synthesis of a 28-mer where a 99% coupling yield per step results in an overall yield of 76% ($.99^{27}$), whereas a 96% yield per step results in an overall yield of only 33% ($.96^{27}$).

Phosphoramidite chemistry, with coupling yields typically greater than 99%, would be a highly desirable approach to phosphorothioate and phosphorodithioate synthesis. However, the phosphite intermediates, which would be sulfurized, are unstable under the conditions of the detrylization step of the reaction cycle. This requires that the phosphite linkage be sulfurized after each coupling step. For practical purposes, such sulfurizations would have to be carried out on an automated synthesizer, but the sulfur precipitation problem discussed above precludes the use of any of the commercially available machines. Moreover, the sulfurization rate of the phosphites is relatively slow and suffers from side reactions that lead to increased contamination of the final product.

In view of the desire to employ phosphorothioate and phosphorodithioate analogs of oligonucleotides as pharmaceutical compounds, it would be advantageous to have available a method for sulfurizing that achieved the highest possible yields of completely sulfurized analogs and that was amenable for use with automated synthesizers, particularly with phosphoramidite and/or phosphorthioamidite chemistries.

SUMMARY OF THE INVENTION

The invention relates to a method of synthesizing sulfur-containing analogs of oligonucleotides, particularly but not exclusively, phosphorothioate and phosphorodithioate analogs. The method of the invention comprises the step of treating phosphorus(III) linkages of the intermediates of the desired analog with a thiuram disulfide to obtain the desired analog. In particular, when phosphoramidite chemistry is employed the phosphorus(III) linkage is a phosphite and the end product is a phosphorothioate, when phosphorothioamidite chemistry is employed the phosphorus(III) linkage is a thiophosphite and the end product is a phosphorodithioate, and when hydrogen phosphonate chemistry is employed the phosphorus(III) linkage is a hydrogen phosphonate diester and the end product is a phosphorothioate.

Preferably, the thiuram disulfides used in the invention are selected from the group consisting of the compounds defined by the following formula:

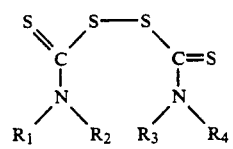

Formula I wherein:

$R_1$, $R_2$, $R_3$, and $R_4$, taken separately are hydrogen, lower alkyl, electron-withdrawing substituted lower alkyl, lower alkyl- or halo-substituted aryl, or a heterocycle containing nitrogen, oxygen, or sulfur and from 5-8 carbon atoms. More preferably, $R_1$, $R_2$, $R_3$, and $R_4$, taken separately, are methyl, ethyl, propyl, isopropyl, n-butyl, sec-butyl, tert-butyl, n-pentyl, cyclopentylmethyl, isopentyl, neopentyl, n-hexyl, neohexyl, isohexyl, cyclohexylmethyl, beta-cyclopentylethyl, nitro, lower alkyl-nitro-, or halo-substituted phenyl, lower alkyl- or halo-substituted benzyl, or lower alkyl-nitro-, or halo-substituted phenylethyl, morpholinyl, thiomorpholinyl, piperidinyl, piperazinyl, beta-electron-withdrawing-substituted ethyl, or the like. In further preference, the electron-withdrawing substituent of beta-electron-withdrawing-substituted ethyl is cyano, nitro, phenylsulphonyl, or phenylester. Most preferably, the beta-electron-withdrawing-substituted ethyl is beta-cyanoethyl. In further preference, the lower alkyl- nitro-, or halo-substituents of the lower alkyl- nitro-, or halo-substituted phenyl and benzyl are methyl, chloro, or bromo. In further preference, morpholinyl, thiomorpholinyl, and piperidinyl are morpholino, thiomorpholino, and piperidino, respectively. Most preferably, $R_1$, $R_2$, $R_3$, and $R_4$, taken separately, are methyl, ethyl, or isopropyl.

$R_1$ and $R_2$ when taken together are cycloalkyl having from 4 to 7 carbon atoms or a heterocycle containing nitrogen, oxygen, or sulfur and from 3 to 6 carbon atoms; more preferably, when taken together, $R_1$ and $R_2$ are cycloalkyl having 4 carbon atoms.

$R_3$ and $R_4$ when taken together are cycloalkyl having from 4 to 7 carbon atoms or a heterocycle containing nitrogen, oxygen, or sulfur and from 3 to 6 carbon atoms; more preferably, when taken together, $R_3$ and $R_4$ are cycloalkyl having 4 carbon atoms.

$R_2$ and $R_3$ when taken together are a bond so that the compound of Formula I is a substituted 1,2-dithio-4,5-diaza heterocycle.

The term "lower alkyl" as used herein denotes straight-chain and branched-chain alkyl groups containing from 1-6 carbon atoms, e.g. methyl, ethyl, propyl, isopropyl, tert-butyl, isobutyl, sec-butyl, neopentyl, tert-pentyl, and the like. "Electron-withdrawing" denotes the tendency of a substituent to attract valence electrons of the molecule of which it is apart, i.e. it is electronegative, March, *Advanced Organic Chemistry*, pgs. 16-18 (John Wiley, N.Y., 1985).

The term "oligonucleotide" as used herein includes linear oligomers of natural or modified nucleosides or of non-nucleosidic analogs linked by phosphodiester bonds or analogs thereof ranging in size from a few monomeric units, e.g. 2-3, to several hundred monomeric units. In particular, the term includes non-natural oligomers having phosphorus-containing linkages whose phosphorus(III) precursors are amenable to sulfurization, e.g. Takeshita et al, J. Biol. Chem., Vo. 282, pgs. 10171-10179 (1987); and Eapienis et al, pgs. 225-230 in, Bruzik and Stec, eds., *Biophosphates and Their Analogs--Synthesis, Structure, Metabolism, and Activity* (Elsevier, Amsterdam, 1986).

DETAILED DESCRIPTION OF THE INVENTION

The invention includes a method of synthesizing phosphorothioates and phosphorodithioates. An important feature of the invention is the step of reacting phosphorus III-containing moieties of oligonucleotide intermediates with a thiuram disulfide to bring about sulfurization. Because thiuram disulfides are efficient sulfurizing agents that do not precipitate out of solution, the invention is particularly useful in the automated synthesis of phosphorothioate and phosphorodithioate analogs of oligonucleotides by all the commercially viable approaches, including hydrogen phosphonate, phosphoramidite, or phosphorothioamidite chemistries.

Detailed procedures for the phosphoramidite, phosphorthioamidite, and hydrogen phosphonate methods of oligonucleotide synthesis are described in the following references, which are incorporated by reference: Caruthers et al, U.S. Pat. Nos. 4,458,066 and 4,500,707; Koester et al, U.S. Pat. No. 4,725,677; Matteucci et al, *J. Amer. Chem. Soc.*, Vol. 103, pgs. 3185-3191 (1981); Caruthers et al, *Genetic Engineering*, Vol. 4, pgs. 1-17 (1981); Jones, chapter 2, and Atkinson et al, chapter 3, in Gait, ed., *Oligonucleotide Synthesis: A Practical Approach* (IRL Press, Washington, D.C., 1984); Froehler et al, *Tetrahedron Letters*, Vol. 27, Pgs. 469-472 (1986); Garegg et al, *Tetrahedron Letters*, Vol. 27, pgs. 4051-4054 and 4055-4058 (1986); Andrus et al, U.S. Pat. No. 4,816,571; Brill et al, J. Am. Chem. Soc., Vol. 111, pgs. 2321- (1989); and Froehler et al, *Nucleic Acids Research*, Vol. 14, pgs. 5399-5407 (1986).

Thiuram disulfides are well known compounds that have many industrial uses, including uses as fungicides, topical antiseptics, and accelerators in the synthesis of rubber. Properties and methods of synthesizing thiuram disulfides are also well known, and are described in the following references which are incorporated by reference: U.S. Pat. No. 1,782,111; U.S. Pat. No. 1,796,977; Nash et al, pgs. 168-191 in Florey, ed. Analytical Profiles of Drug Substances, Vol. 4 (Academic Press, N.Y., 1975); Cummings et al, Indust. Eng. Chem., Vol. 20, pgs. 1173-1176 (1928); and World Health Organization, pgs. 225-236 in IARC Monographs on the Evaluation of Carcinogenic Risk of Chemicals to Man, Vol. 12 (1976). As indicated by these references, thiuram disulfides are synthesized in several different ways, including by the oxidation of the dimethylamine salt of dimethyldithiocarbamic acid with iodine in an ethanolic solution, e.g. von Braun, I. Chem. Ber., Vol. 35, pgs. 817-829 (1902), by passing chlorine gas through a solution of sodium dimethyldithiocarbamate, e.g. Wenyon, pgs. 621-623 in Chemical Technology: An Encyclopedic Treatment, Vol. 4 (Barnes and Noble, New York, 1972), or by oxidation of sodium dimethyldithiocarbamate with hydrogen peroxide or iodine, e.g. Spencer, Guide to the Chemical Used in Crop Protection, 6th Ed., University of Western Ontario, Publication 1093 (London, Ontario, 1973).

When employed as a sulfurizing agent in the hydrogen phosphonate approach, a thiuram disulfide is delivered to the completed oligonucleotide chain in a suitable organic solvent, such as acetonitrile, tetrahydrofuran, dichloromethane, or the like, in a concentration of between about 0.01M to about 2.0M. Preferably, the sulfurization is accomplished on an automated DNA synthesizer, e.g. an Applied Biosystems model 380B, or like machine.

Most preferably, thiuram disulfides are employed as a sulfurizing agents in the phosphoramidite or phosphorthioamidite approaches. A thiuram disulfide is delivered to the growing oligomer as a separate step within each addition cycle. Generally, the addition cycles of these methods of synthesis involve the following steps: (1) deblocking a blocked functionality (usually a 5'-tritylated hydroxyl) on the growing correct-sequence chain, or on the initial monomer attached to a solid phase support, to form a reactive functionality (e.g. a 5'-hydroxyl), (2) reacting a blocked and protected nucleoside phosphoramidite or phosphorthioamidite monomer or analog thereof (usually in the presence of an activator, e.g. tetrazole) with the reactive functionality of the growing correct-sequence chain, (3) capping unreacted reactive functionalities, and (4) oxidizing the newly formed phosphorus(III) linkage to form the naturally occurring pentacoordinate state. The sequence of above steps (3) and (4) can be reversed. The term "protected" in reference to monomer, particularly nucleoside phosphoramidites or phosphorthioamidites, means that moieties such as exocyclic nitrogens, 2'-hydroxyls, oxygens bonded to the phosphorous, or the like, have protection groups (usually base-labile) attached which are removed after synthesis is completed, e.g. as those described in Koester et al (cited above), or in Molko et al, European patent publication no. 241,363 dated Oct. 14, 1987. The term is also meant to include monomers which may not have moieties requiring protective groups, e.g. some nucleoside analogs, abasic nucleosides, and the like. In the method of the invention, thiuram disulfides are employed as sulfurizing agents in place of the oxidation step. Preferably, a thiuram disulfide is delivered to the growing oligomer in a suitable organic solvent, such as acetonitrile, tetrahydrofuran, dichloromethane, or the like, in a concentration of between about 0.01M to about 2.0M. Preferably, the step of sulfurizing with a thiuram disulfide is accomplished on an automated DNA synthesizer. In both approaches a wide variety of reaction temperatures may be used. Preferably, the sulfurization is carried out at a temperature in the range of 0° C. to 100° C., and more preferably, in the range of 15° C. to 60° C.

EXAMPLE

Synthesis of a 22-base Phosphorothioate Oligonucleotide Using Tetraethylthiuram Disulfide as Sulfurizing Agent A 22-base phosphorothioate oligonucleotide, 5'-CTTCGATCATCGGTATGCTCCT, was synthesized by the phosphoramidite method on an automated synthesizer, on which the reaction vessel was modified by wrapping it with a resistive heating element with integral RTD (Watlo, St. Louis, Mo.) to provide control of reaction temperature. The heating element was connected to an Omron temperature controller with an external relay tape to provide control of reaction temperature. The standard synthesis protocol was followed, except that in place of the oxidation step, a sulfurization step was substituted. In other words, the synthesis consisted of repeated cycles of detritylization, coupling, sulfurization, and capping. Separation of the final product from the synthesis column and purification were accomplished by standard means. The sulfurization step was accomplished by exposing the growing chain to 0.55M tetraethylthiuram disulfide (Aldrich, Milwaukee, Wis.) in acetonitrile at 50° C. for 15 minutes. The tetraethylthiuram disulfide can be conveniently recrystallized from acetonitrile; however, no difference was noted in results using recrystallized material or material as supplied by the manufacturer.

The yield of trityl cation released during the detritylization steps averaged 99%. The trityl yield is a both a measure of coupling efficiency and a measure of the extent of sulfurization, since non-sulfurized (or oxidized) trivalent phosphorus linkages in the oligonucleotide are labile to cleavage during detritylization.

The 22-mer was cleaved from the support and deprotected with concentrated ammonium hydroxide at 55° C. for 3 hours. The 31P-NMR spectra (JEOL, 36.5 MHz, ppm vs $H_3PO_4$ external reference) of the product showed greater than 98% sulfur incorporation (55.1 ppm) with less than 2% oxygen incorporation (−1.1 ppm).

What is claimed is:

1. In a method for synthesizing a sulfurized oligonucleotide, the method of the type wherein a phosphorus-(III) linkage of an oligonucleotide intermediate is sulfurized to form a phosphorus(V) linkage wherein a sulfur atom is covalently bonded in a non-bridging position to a phosphorus atom of said phosphorus(V) linkage, an improvement comprising:
   sulfurizing the phosphorus(III) linkage of the oligonucleotide intermediate by exposing the oligonucleotide intermediate to a thiuram disulfide at a temperature within the range of 0–100° C.

2. The method of claim 1 wherein said thiuram disulfide is defined by the formula:

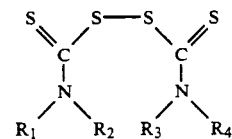

wherein:
$R_1$, $R_2$, $R_3$, and $R_4$, taken separately, are selected from the group consisting of alkyl having from 1 to 6 carbon atoms; halo-, nitro-, or cyano-substituted alkyl having from 1 to 6 carbon atoms; and a heterocycle containing from 5–8 carbon atoms and a heteroatom selected from the group consisting of nitrogen, oxygen, or sulfur;

$R_1$ and $R_2$ when taken together are selected from the group consisting of cycloalkyl having from 4 to 7 carbon atoms and a heterocycle containing from 3 to 6 carbon atoms and a heteroatom selected from the group consisting of nitrogen, oxygen, and sulfur;

$R_3$ and $R_4$ when taken together are selected from the group consisting of a cycloalkyl having from 4 to 7 carbon atoms and a heterocycle containing from 3 to 6 carbon atoms and a heteroatom selected from the group consisting of nitrogen, oxygen, and sulfur; and $R_2$ and $R_3$ when taken together are a bond so that said thiuram disulfide is a substituted 1,2-dithio-4,5-diaza heterocycle.

3. The method of claim 2 wherein:
$R_1$, $R_2$, $R_3$, and $R_4$, taken separately, are selected from the group consisting of methyl; ethyl; propyl; isopropyl; n-butyl sec-butyl; tert-butyl; n-pentyl; cyclopentylmethyl; isopentyl; neopentyl; n-hexyl; neohexyl; isohexyl; cyclohexylmethyl; beta-cyclopentylethyl; lower alkyl-, nitro-, or halo-substituted phenyl; lower alkyl-, nitro-, or halo-substituted benzyl; lower alkyl-, nitro-, or halo-substituted phenylethyl; morpholinyl; thiomorpholinyl; piperidinyl; and piperazinyl;

$R_1$ and $R_2$ when taken together are cycloalkyl having 4 carbon atoms; and $R_3$ and $R_4$ when taken together are cycloalkyl having 4 carbon atoms.

4. The method of claim 3 wherein $R_1$, $R_2$, $R_3$, and $R_4$, taken separately, are selected from the group consisting of methyl, ethyl, and isopropyl.

5. The method of claim 4 wherein said step of sulfurizing includes forming phosphorothioate or phosphorodithioate linkages from said phosphorus(III) linkages.

* * * * *